United States Patent
Kirpotin et al.

[11] Patent Number: 5,980,935
[45] Date of Patent: *Nov. 9, 1999

[54] CATIONIC LIPIDS AND METHODS OF USE THEREFOR

[76] Inventors: Dmitri Kirpotin, 435 43rd Ave., Apartment 102, San Fransisco, Calif. 94121; Daniel C. F. Chan, 3691 S. Quebec St., Denver, Colo. 80237; Paul Bunn, 630 Sundown La., Evergreen, Colo. 80439

[*] Notice: This patent issued on a continued prosecution application filed under 37 CFR 1.53(d), and is subject to the twenty year patent term provisions of 35 U.S.C. 154(a)(2).

[21] Appl. No.: 08/648,558
[22] Filed: May 15, 1996
[51] Int. Cl.$^6$ ..................................................... A61K 9/127
[52] U.S. Cl. .............................................. 424/450; 935/54
[58] Field of Search ............................. 424/450; 554/53; 935/54

[56] References Cited

U.S. PATENT DOCUMENTS

| | | | |
|---|---|---|---|
| 4,559,324 | 12/1985 | Fujino | 514/14 |
| 4,804,559 | 2/1989 | Guo | 424/450 |
| 5,264,618 | 11/1993 | Felgner et al. | 514/7 |
| 5,286,634 | 2/1994 | Stadler et al. | 435/172.3 |
| 5,364,884 | 11/1994 | Varma | 514/551 |
| 5,459,127 | 10/1995 | Felgner et al. | 514/7 |
| 5,614,503 | 3/1997 | Chaudhary et al. | 514/44 |

OTHER PUBLICATIONS

Debs et al., 7 *Am J Respir Cell Mol Biol* 406 (1992).
Hui et al., 71 Biophysical Journal 590 (1996).
Farhood et al, Annals New York Acad. Sciences 23 (199_).
Leventis and Silvius, 1023 Biochimica et Biophysica Acta 124 (1990).
Lee et al, 7 Human Gene Therapy 1701 (1996).
Puyal et al, 228 J. Biochem 697 (1995).
Brunette et al, 20(5) Nucleic Acids Res. 1151 (1991).
Guo et al, 3(1) J. Liposome Res. 51 (1993).
Remy et al., 5 *Bioconjugate Chem.* 647 (1995).
Behr, 5 *Bioconjugate Chem.* 382 (1994).
Gershon, et al., 32 *Biochemistry* 7143 (1993).
Chang & Brenner, citation unknown.

*Primary Examiner*—Gollamudi S. Kishore
*Attorney, Agent, or Firm*—Kristine H. Johnson; Macheledt Bales & Johnson LLP

[57] ABSTRACT

The present invention relates generally to a non-toxic lipid conjugated with a cationic amino acid containing a guanidino group. Specifically, the naturally-occuring lipid DOPE is combined with the naturally-occurring amino acid Arginine. These compounds are useful for encapsulating and delivering pharmaceuticals and poly and oligonucleotides. These compound improve over current compounds, because they are composed of non-toxic and, in the case of Arg-DOPE, natural components, and therefore result in minimal unwanted side effects. Methods of use of the cationic lipids are also claimed.

16 Claims, 5 Drawing Sheets

Expression of luciferase reporter gene in C26 cells transfected with complexes of pCMVLUC with various cationic lipids.

Expression of luciferase reporter gene in C26 cells transfected with complexes of pCMVLUC with various cationic lipids.

Expression of luciferase reporter gene in H1048 cells transfected with complexes of pCMVLUC with various cationic lipids.

Expression of luciferase reporter gene in KB31 cells transfected with complexes of pCMVLUC with various cationic lipids.

CATIONIC LIPIDS AND METHODS OF USE THEREFOR

BACKGROUND OF THE INVENTION

1. Field of the Invention

The present invention relates generally to a non-toxic lipid conjugated with a cationic amino acid containing a guanidino group. Specifically, the naturally-occuring lipid dioleoylphosphatidylethanolamine (DOPE) is combined with the naturally-occurring amino acid Arginine. These compounds are useful for encapsulating and delivering pharmaceuticals and poly and oligonucleotides. These compounds improve over current compounds, because they are composed of non-toxic and, in the case of Arginine conjugated with DOPE (Arg-PE), natural components, and therefore result in minimal unwanted side effects. Methods of use of the cationic lipids are also claimed.

2. Background of the Invention

Cationic lipids have been described in the past. Most of the cationic lipids previously described involve synthetic (non-naturally-occurring) components. The three patents provided in this background to the invention also describe many non-naturally-occurring components.

Stadler, et. al., U.S. Pat. No. 5,286,634 describes a process for transferring nucleic acids into cells, most particularly plant cells, using a polycationic compound in conjunction with a cationic lipid.

Felgner, et. al., U.S. Pat. No. 5,264,618 describes several cationic lipids, but is limited to those with an ammonium group. The present cationic lipid does not utilize an ammonium group.

Feigner, et al., U.S. Pat. No. 5,459,127 is a continuation of the above patent, and claims the formulations and methods of the patent above.

Gershon, et al., 32 *Biochemistry* 7143 (1993). This journal article describes a theory of a mechanism of action for the transfer of nucleic acids via cationic liposomes. Although it discusses PE (a naturally-occurring lipid), it does not describe it in conjunction with arginine.

Behr, 5 *Bioconjugate Chem.* 382 (1994) is a review article which describes many cationic lipids, but not a Arg-PE construct.

Remy et al., 5 *Bioconjugate Chem.* 647 (1995) is an article following-up the article above, in the same journal. It describes DOPE conjugated with spermine. It does not disclose an Arg-PE construct.

Chang & Brenner, citation unknown, describes protocols for transferring cationic liposomes into cells. It does not disclose the Arg-PE construct.

SUMMARY OF THE INVENTION

It is therefore an object of the present invention to provide cationic lipids which are useful for relatively non-toxic delivery of substances into cells.

Specifically, it is an object of the present invention to provide the cationic lipid Arg-PE.

It is a further object to provide methods to transfer substances into cells via the cationic lipids disclosed.

Other objects and features of the present invention will be apparent from the following detailed description of the invention.

DETAILED DESCRIPTION OF THE INVENTION

Figure 1:
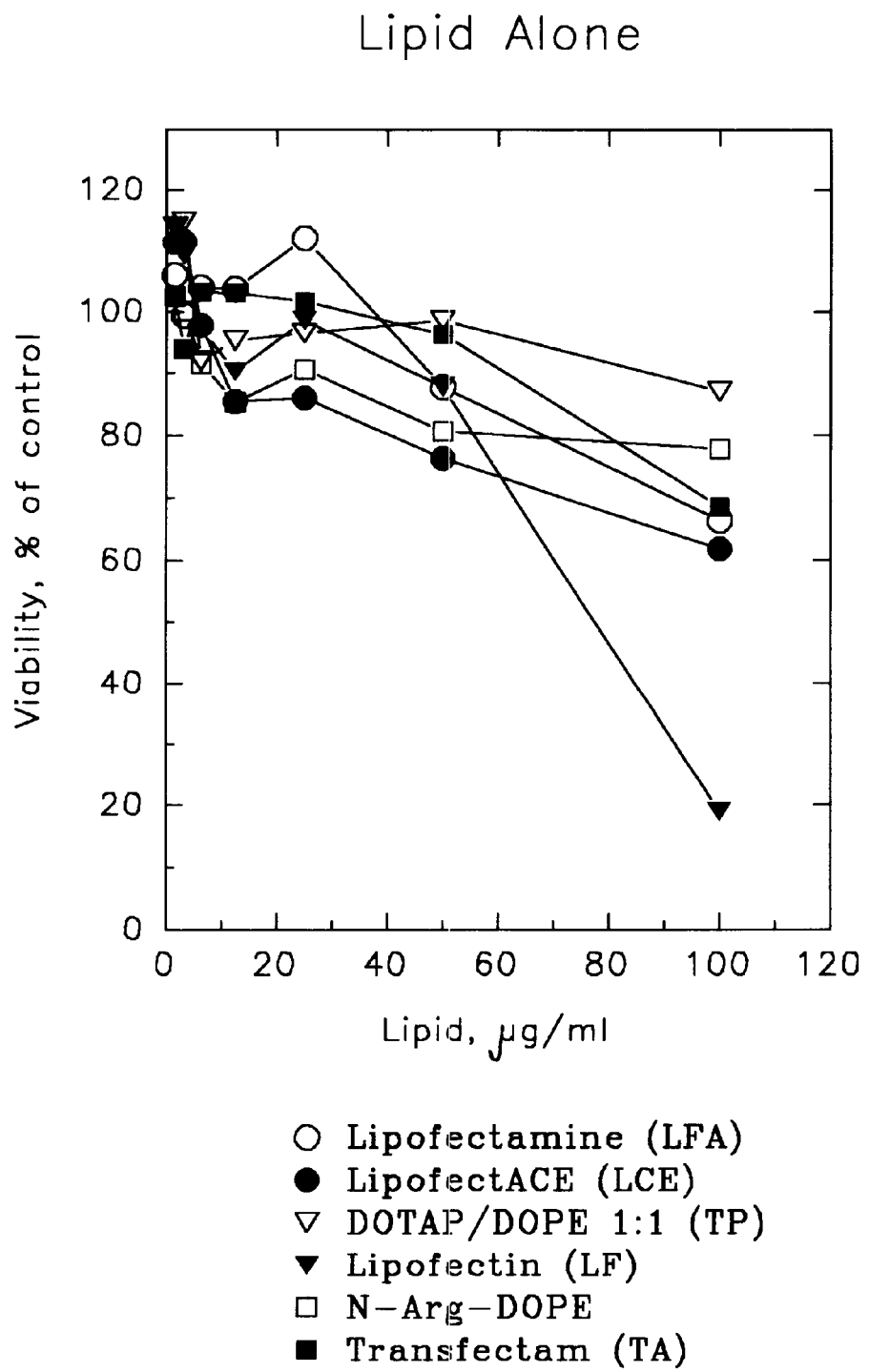
FIG. 1. Effect of Arg-PE and commercially available cationic lipids on the growth of cultured KB31 cells using lipids alone.

This invention relates, inter alia, to materials used in facilitating the delivery of nucleic acids and oligonucleotides into living cells. The utility of such delivery is recognized in the practice of biomedical research and industry, biotechnology, and medicine.

Specifically, the use of cationic lipids for facilitating the entry of functional nucleic acids and oligo nucleotides into living cells has been described in the scientific and patent literature. The array of molecular structures of such lipids, as reviewed, for example, in Remy, cited above, and Behr, cited above, demonstrates that cationic properties of such lipids have been provided by introduction of a positively-charged group, or groups, based on the ammonium function. However, ammonium group (pK 9.2) is a weaker base than guanidine group (pK 12.7) present in the natural protein amino acid arginine, while the use of strong bases such as quaternary ammonium groups renders a molecule of cationic lipid more toxic and less biodegradable by the cell. It is also noteworthy that protamines, natural polypeptides with the highest DNA-compacting ability, have about 60% arginine content.

An underlying concept of the present invention is to employ a guanidine-bearing group with an arginine residue in an amphipatic construct as a candidate for a nucleic acid cellular delivery vehicle which would be readily degraded by cellular enzymes, and fragments resulting from such degradation would be natural ubiquitous metabolites of a cell. In one aspect of the invention, the hydrophilic arm has charged groups, (either negative or zwitterionic in nature), which are useful for forming bilayers in the physiological pH and ionic environment. Liposomal delivery is therefore more advantagous using the present invention. Most specifically, a compound which bears a phosphatidyl group is disclosed in the present invention. For example, N-L-Arginyl-phosphatidyl-ethanolamine is provided by the present invention.

In a practical embodiment of the above-described inventive concept, we have conjugated arginine to a natural phospholipid, phosphatidylethanolamine (PE), by forming an amide linkage between the amino group of PE and carboxy group of arginine. The resulting molecule, N-arginyl-PE (Arg-PE) has the following structure:

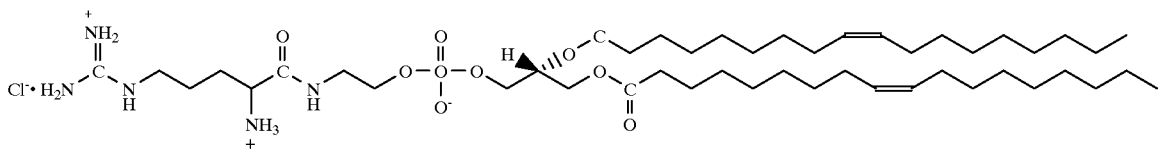

This compound possesses a net cationic charge due to the presence of one acidic and two basic groups, one of the latter being a guanidine group of the arginyl residue. This molecule would be easily split by cellular peptidases into its original components, arginine and PE, both of which are natural cellular constituents.

We have tested Arg-PE for its ability to deliver functional plasmid DNA and phosphorothioate oligonucleotide (PS ON) into living cells. We have also compared this material with an array of comparable materials available commercially. The test showed higher efficiency of the cellular delivery of DNA and PS ON by the invented lipid. It was our unexpected finding that the invented lipid, being essentially a monocationic lipid (bearing the positive net molecular charge equal to one) had the efficiency of DNA delivery superior to that of a polycationic lipid, DOGS, which was reported to have better DNA delivery properties than any of the known monocationic lipids. (Remy and Behr, each cited above.) The inventive lipid was highly active for the DNA delivery into the cells even without the use of a "helper lipid". Helper lipids are required for the activity of previously known monocationic lipids.

Toxicity of most currently available cationic lipids is a limiting factor in their practical uses. We have compared the toxicity of the invented lipid and of the array of commercially available cationic lipids, alone or in combination with DNA for the cultured human cells. This study showed that the invented monocationic lipid Arg-PE has no detectable toxicity in the studied range of concentrations efficient for gene delivery, the property found, again, only in its polycationic counterpart, DOGS, and not generally expected in a monocationic lipid.

The details of the above experiments and others are given in the Examples below.

Therefore, we have prepared the invented material and demonstrated that it meets the purposes of the invention, also showing some unexpected, useful properties that made it superior to the currently available constructs.

It is recognized that the present invention is not limited to the above-described embodiment, Arg-PE, which is merely an example of possible embodiments. More broadly, the invention covers a group of materials whose molecules are capable of bearing a net cationic charge in an aqueous solution and are capable of being degraded in the living cells into non-toxic, metabolizable fragments comprising (1) a guanidino domain as a bearer of the cationic charge; (2) a hydrophobic domain capable of causing the molecule to form micellular structures in aqueous medium and (3) a hydrophilic arm linking together the above two domains.

The delivery of poly-and oligonucleotides into living cells by the invented material uses the same procedure as described in the prior art. Specifically, the invented lipids may be formulated alone, or in the mixture with other (non-cationic) lipids, or even combined with other cationic lipids, in the form of micellular solution, or bilayer vesicles (liposomes), in an aqueous medium, and brought into contact with a polynucleotide (DNA or RNA), or oligonucleotide, prior to administration to the cells. Alternatively, the lipid may be formulated as a solution in a water-miscible organic solvent, such as ethanol, and combined with the poly or oligonucleotide in an aqueous medium prior to administration to the cells.

The invented materials alone are capable of forming bilayer vesicles (liposomes) in an aqueous buffer. Since cationic liposomes are known to be the instruments for intracellular delivery of substances other than nucleic acids (Debs et.al., 265 J. Biol. Chem. 10189 (1990)), the liposomes formed by the invented lipids have utility for the cellular delivery of substances other than poly-or oligonucleotides, such as, for example, proteins and various pharmaceuticals. The present invention therefore provides methods for treating various disease states, so long as the treatment involves transfer of material into cells. In particular, treating the following disease states using the present invention is included within the scope of this invention: cancer, infectious diseases, inflammatory diseases and genetic hereditary diseases.

Is to be noted that certain changes and modifications are apparent to those skilled in the art. Such changes and modifications are to be understood as included within the scope of the present invention as defined by the appended claims.

EXAMPLES

1. Synthesis of N-Arginyl-dioleoylphosphatidylethanolamine (Arg-PE) (method 1)

75 mg (0.101 mmol) of dioleoylphosphatidylethanolamine (Avanti Polar Lipids, USA) (DOPE), 34.3 mg (0.110 mmol) of $N^{alpha}$-tret-butoxycarbonyl-arginine hydrochloride (Sigma, USA), 24.8 mg (0.129 mmol) of N-ethyl-N'-dimethylaminopropyl-carbodiimide hydrochloride (Sigma, USA), and 14.9 mg (0.129 mmol) of N-hydroxysuccinimide (Sigma, UAS) were dissolved in 2 ml of chloroform and incubated with agitation at 37° C. for 3 hours. At that point, TLC ($CHCl_3$—$CH_3OH$—$H_2$ 65:25:4, silica) showed 100% conversion of DOPE ($R_f$ 0.49) into faster moving, ninhydrin-negative product ($R_f$ 0.69), identified as N-($N^{alpha}$-tret-butoxycarbonyl-arginyl)-DOPE. This product was purified by chromatography on silica and deprotected by treatment with 4M HCl in anhydrous dioxane for 3 hours. After removal of volatiles in vacuum, the residue was chromatographed on silica, eluent $CHCl_3$—$CH_3OH$ 7:3, to obtain Arg-PE ($R_f$ 0.26 in the above system) with the yield of 10.8 mg (12% of theory). Phosphate to primary amino group ratio: Theory 1.0, Found 0.90±0.12.

2. Synthesis of Arg-PE (Method 2)

56.5 mg (0.182 mmol) of $N^{alpha}$-tret-butoxycarbonyl-arginine hydrochloride, 26.3 mg (0.229 mmol) of N-hydroxysuccinimide, and 44 mg (0.210 mmol) of dicyclohexyl cadbodiimide were stirred in 0.7 ml of anhydrous chloroform at room temperature for 3 hours and then at 4° C. for 1 hour. The precipitate of urea was removed by filtration, and the filtrate was added to 110.3 mg (0.148 mmol) of DOPE, and 0.04 ml of anhydrous triethylamine in 0.3 ml of chloroform. After 6 hours at room temperature, the product was chromatographed on silica using chloroformmethanol (7:3). Fractions containing N-(N$^{-alpha}$-tret-butoxycarbonyl-arginyl)-DOPE were combined and brought to dryness in vacuum. The dry residue was deprotected with 4 N HCl/dioxane as described in the Example 1, and the final product was purified by chromatography. Yield of Arg-PE:33.5 mg (24% of theory). Molar ratio of phosphate to primary amino group: theory, 1.0; found 0.88±0.08.

3. Formulation of Arg-PE into Aqueous Micellular Solution

An aliquot of chloroform solution containing 3 mg of Arg-PE was evaporated to dryness in vacuum. The residue was dispersed by gentle shaking in 3 ml of 0.15 M NaCL containing 5 mM HEPES, pH 7.4 (HEPES-NS), cooled in an ice-water bath, and treated with ultrasound for 5 minutes. The resulting clear solution was sterilized by filtration through a 0.2 micrometer cellulase acetate filter.

4. Formulations of Commercial Cationic Lipids

Lipofectin, Lipofectamine, and Transfectam are registered trademarks of Gibco BRL, USA. These materials were used as supplied from the manufacturer. DOTAP-DOPE 1:1 was prepared from the mixture (1:1 by weight) of 1,2 dioleoyloxy-3-trimethylammoniopropane (DOTAP, Avanti PolarLipids, USA) and DOPE by dissolving in distilled water at the concentration 2 mg/ml. DDAB-DOPE 1:2.5 (also known as LipofectACE®, Gibco BRL, USA) was prepared from the mixture of dioctadecyl-dimethylammonium bromide (DDAB, Sigma, USA) and DOPE in the weight ratio 1:2.5 dissolved in distilled water at the concentration of 3 mg/ml with brief sonication. All lipid solutions were sterilized by filtration though 0.2 micrometer cellulase acetate filter, unless supplied sterile by manufacturers.

5. Delivery of Bacterial Plasmid into K-B Cells

Figure 5:
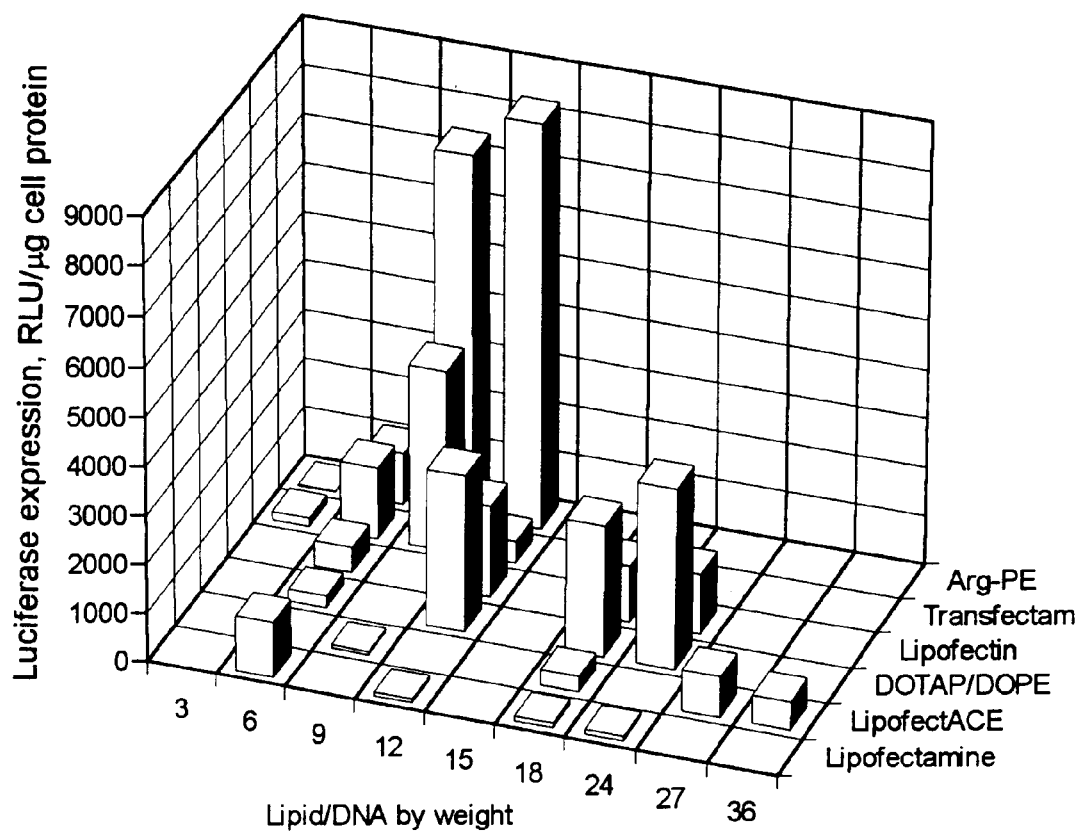
FIG. 5. Expression of luciferase reporter gene in KB31 cells transfected with complexes of pCMVLUC with various cationic lipids.

Human epidermoid carcinoma (KB31) cells were grown at 37° C. and 5% $CO_2$ in RPMI 1640 medium supplemented with 10% heat-inactivated fetal calf serum. The cells were plated into a 12-well cell culture plate at $1.5 \times 10^5$ cells/well in 1 ml of the growth medium. After a 24 hour acclimation period, 1 microgram of bacterial plasmid (pUC-CMVLUC) with luciferase reporter gene under control of the CMV promoter was added to the cell media, either alone, or in the complex with cationic lipids as indicated below, prepared at a variety of lipid-to-DNA ratios. The complexes were prepared by mixing the lipid, as supplied by the manufacturer, and 1 microgram of the plasmid in 40 microliters of HEPES-NS. Seven hours later, the plasmid containing medium was replaced with HEPES at pH 7.4 (HEPES-BSS), harvested using 3 mM EDTA in HEPES-BSS, lysed by freezing and thawing in 0.1 ml of 0.1 M potassium phosphate, pH 7.8, containing 1 mM DTT, and centrifuged to obtain cell extracts. The extracts were assayed for luciferase by luminometry and for total protein using protein dye method (Bio-Rad, USA). The results are displayed in FIG. 5 and Table 1.

TABLE 1

Comparative expression of LUC gene in KB cells transfected with pUC-CMVLUC plasmid alone or in a complex with Arg-PE or commercially available cationic lipids

| Lipid | Range of plasmid/lipid ratios studied | Maximum luciferase activity, RLU/mg protein | Plasmid/lipid ratio at maximum luciferase activity |
| --- | --- | --- | --- |
| None | NA | Undetectable | NA |
| DOTAP-DOPE 1:1 | 1:6–1:24 | $3.21 \times 10^6$ | 1:12 |
| Transfectam ® | 1:3–1:12 | $3.70 \times 10^6$ | 1:9 |
| Lipofectin ® | 1:6–1:24 | $1.88 \times 10^6$ | 1:12 |
| Lipofectamine ® | 1:6–1:24 | $1.13 \times 10^6$ | 1:6 |
| DDAB–DOPE 1:2.5 | 1:9–1:36 | $8.35 \times 10^5$ | 1:27 |
| Arg-PE | 1:3–1:12 | $8.25 \times 10^6$ | 1:12 |

6. Toxicity of Arg-PE and Commercially Available Lipids for Cultured KB31 Cells

Figure 2:
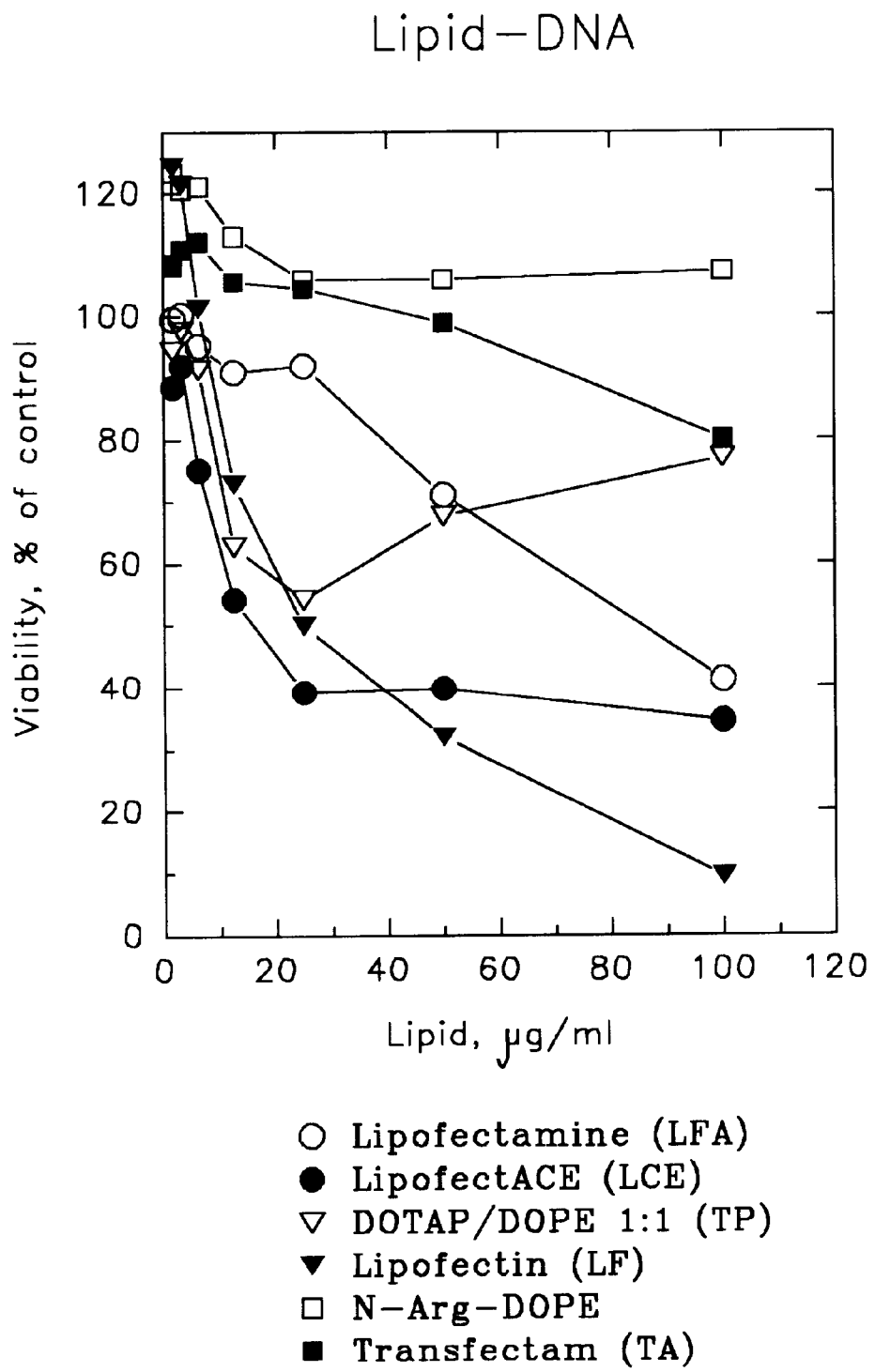
FIG. 2. Effect of Arg-PE and commercially available cationic lipids on the growth of cultured KB31 cells using lipid-DNA complexes. DNA/lipid ratios are 1:18 for LFA, TP, LF; 1:9 for TA, Arg-PE; 1:27 for LCE.

Cells were grown as described in Example 4, plated at $5 \times 10^3$/well in 96-well cell culture plates, and acclimated for 48 hours. Lipids alone, or in the complex with pUC-CMVLUC plasmid at the indicated ratio were added to the cell medium at concentrations of 3.2–100 microgram of lipid per 1 ml of growth medium. After 24 hours exposure to the lipids, the lipid-containing media were removed, and the cells were further incubated in fresh growth medium for 65 hours. At the end of incubations, the cell viability was determined by MTT assay as described in T. Mossman 65 *J. Immunol. Methods* 55 (1983). The results are shown in FIGS. 1 and 2. Arg-PE displayed the least toxicity when given either as such or in the form of DNA-lipid complexes.

7. Delivery of a Phosphorothioate Oligonucleotide into the Cells Via Complexes with Arg-PE and Commercial Cationic Lipids Human small cell lung carcinoma cells (NCI-H1048) were grown in RPMI-1640 medium with 10% heat-inactivated fetal calf serum. The cells were exposed for 7 hours in a serum-free medium with a fluorescein-labeled 24-mer phosphorothioate oligonucleotide (0.5 micro-M final concentration), alone or in a complex with lipids obtained as described in Examples 2 and 3. Then the equal volume of serum-supplemented medium was added, and the cells were incubated for another 18 hours. After incubation, cellular accumulation of the oligonucleotide was assayed by flow cytometry using fluorescein label fluorescence. The results are shown in Table 2, below. The results indicate that Arg-PE enhanced the uptake of the oligonucleotide by the cells at least as effectively as the tested commercial cationic lipids.

TABLE 2

Effect of Arg-PE and some commercial lipids on the uptake of fluorescein-labeled phosphorothioate oligonucleotide by cultured NCI-H1048 cells

| Lipid, oligo/ lipid ratio | Total uptake: mean cell fluorescence, relative units | Uptake increase over oligo alone, times |
| --- | --- | --- |
| None | 0.698 | NA |
| Lipofectin ®, 1:4 | 3.53 | 5.06 |
| Lipofectamine ®, 1:4 | 2.19 | 3.14 |
| | 2.97 | 4.26 |
| Arg-PE, 1:6 | 4.08 | 5.85 |

8. Uptake of Fluorescent-Labeled Phosphorothioate Oligonucleotide by Human Cancer Cells In Vitro Human lung adenocarcinoma cells (NCI-A549, American Type Culture Collection) were grown on Permanox® chamber slides in RPMI 1470 medium supplemented with 10% fetal calf serum (R-10) at 37° C. and 5% $CO_2$. 4 micrograms of fluroscein-labeled 18-mer phosphorothioate oligonucleotide (F-ON) in 0.1 ml of HEPES-buffered saline (20 mM hydroxyethylpiperazine-ethane sulfonic acid (HEPES), 144 mM NaCl, pH 7.4) were mixed with Arg-PE formulated as described in Example 2, at the weight ratio of oligonucleotide to the lipid of 1:12. After 30 minutes of incubation, the mixture was made up to 2 mi with R-10 and added to the cells. After 24 hours incubation at 37° C., 5% $CO_2$, the medium was aspirated, the cells washed 4 times with HEPES-buffered balanced salt solution, and immediately examined through a fluorescence microscope. The microscopic examination showed bright green nuclear fluorescence and substantial cytoplasmic deposits of granular fluorescent material in 100% of the cells. Accumulation of the oligonucleotide in NCI-A549 cells, incubated with F-ON under the same conditions, but in the absence of Arg-PE, was undetectable.

9. Delivery of Bacterial Plasmid into Mouse Colon Carcinoma Cells

Figure 3:
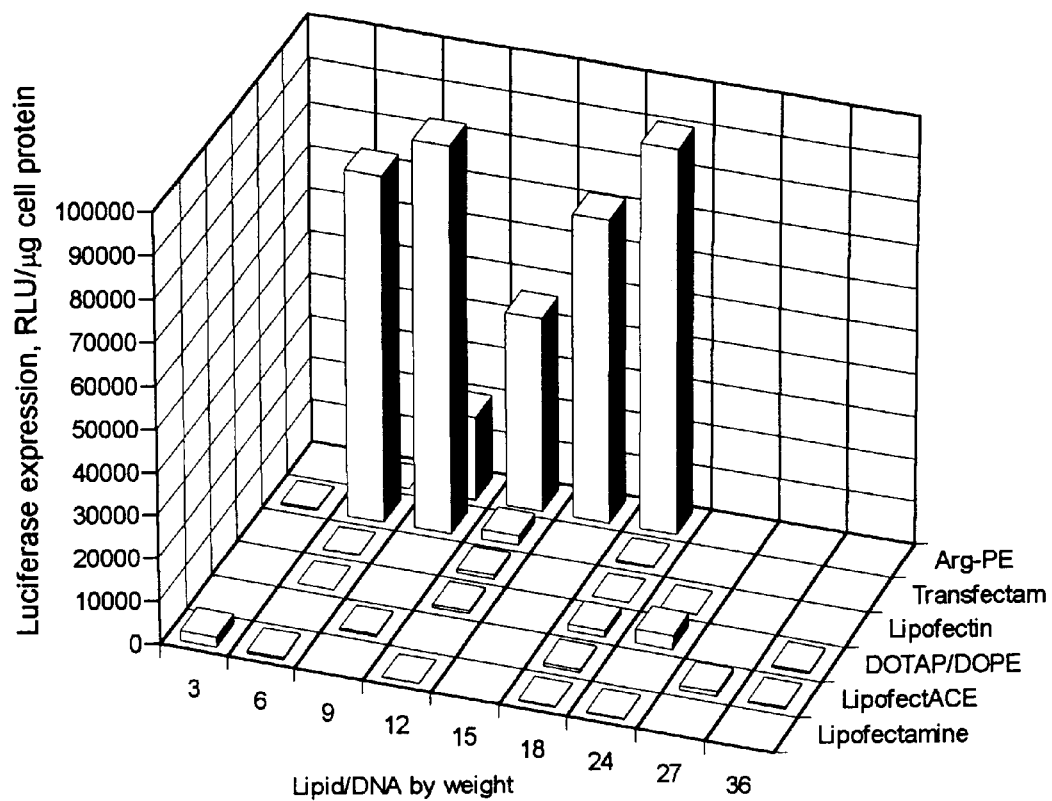
FIG. 3. Expression of luciferase reporter gene in C26 cells transfected with complexes of pCMVLUC with various cationic lipids.

Mouse colon carcinoma cells (C26) were grown, incubated with plasmid pCMVLUC in the presence of Arg-PE or commercially available cationic lipids, and assayed for luciferase expression as described in Example 5 above. The following results were obtained, indicating that Arg-PE was more effective for the plasmid delivery into C26 cells than other monocationic lipids and as effective as the polycationic lipid Transfectam®. Results are shown in FIG. 3 and Table 3.

10. Delivery of Bacterial Plasmid into Human Small Cell Carcinoma Cells

Figure 4:
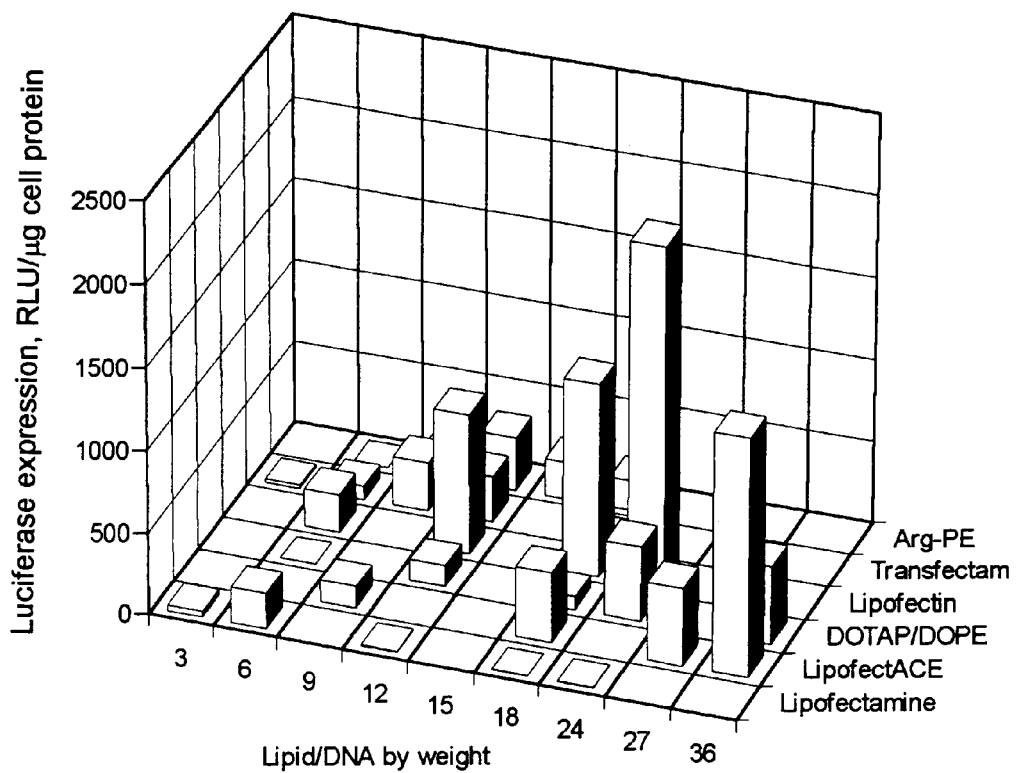
FIG. 4. Expression of luciferase reporter gene in H1048 cells transfected with complexes of pCMVLUC with various cationic lipids.

Human extrapulmonary small cell carcinoma cells (NCI-H1048), American Type Culture Collection) were grown, incubated with plasmid pCMVLUC in the presence of Arg-PE or commercially available cationic lipids, and assayed for luciferase expression as described in the Example 5 above. The following results were obtained, indicating that Arg-PE was as effective for the plasmid delivery into NCI-H1048 cells as a polycationic Transfectam®. Results are shown in FIG. 4 and Table 4.

TABLE 4

Comparative expression of LUC gene in NCI-H1048 cells transfected with pUC-CMVLUC plasmid alone or in a complex with Arg-PE or commercially available cationic lipids

| Lipid | Range of plasmid/lipid ratios studied | Maximum luciferase activity, RLU/mg protein | Plasmid/lipid ratio at maximum luciferase activity |
|---|---|---|---|
| None | NA | Undetectable | NA |
| DOTAP-DOPE 1:1 | 1:6–1:36 | $4.76 \times 10^5$ | 1:36 |
| Transfectam ® | 1:3–1:18 | $2.97 \times 10^5$ | 1:9 |
| Lipofectin ® | 1:6–1:24 | $2.07 \times 10^6$ | 1:24 |
| Lipofectamine ® | 1:6–1:24 | $2.16 \times 10^5$ | 1:6 |
| DDAB-DOPE 1:2.5 | 1:9–1:36 | $1.45 \times 10^6$ | 1:36 |
| Arg-PE | 1:3–1:18 | $3.21 \times 10^5$ | 1:12 |

What is claimed is:

1. A micellar or liposomal composition for enhancing delivery of nucleic acids into cells comprising: at least one nucleic acid, a first moiety and optionally a second moiety,
   wherein said first moiety comprises (a) a guanidino domain of the amino acid arginine; (b) a hydrophobic domain capable of causing the molecule to form micellar or liposomal structures in aqueous medium; and (c) a linker joining the guanidino domain and the hydrophobic domain, said linker being a zwitterion in aqueous medium at neutral pH; and
   wherein said second moiety is selected from the group consisting of DOPE and cholesterol; and
   wherein the first moiety is 90 to 100 molar percent and the second moiety is 0 to 10 molar percent of the sum of the total of the first and second moiety, wherein said nucleic acid is incorporated within the micellar or liposomal structures.

TABLE 3

Comparative expression of LUC gene in C26 cells transfected with pUC-CMVLUC plasmid alone or in a complex with Arg-PE or commercially available cationic lipids

| Lipid | Range of plasmid/lipid ratios studied | Maximum luciferase activity, RLU/mg protein | Plasmid/lipid ratio at maximum luciferase activity |
|---|---|---|---|
| None | NA | Undetectable | NA |
| DOTAP-DOPE 1:1 | 1:6–1:36 | $3.11 \times 10^6$ | 1:24 |
| Transfectam ® | 1:3–1:18 | $9.08 \times 10^7$ | 1:9 |
| Lipofectin ® | 1:6–1:24 | $8.88 \times 10^5$ | 1:12 |
| Lipofectamine ® | 1:6–1:24 | $2.333 \times 10^6$ | 1:3 |
| DDAB-DOPE 1:2.5 | 1:9–1:36 | $1.16 \times 10^6$ | 1:27 |
| Arg-PE | 1:3–1:18 | $9.02 \times 10^7$ | 1:18 |

2. A composition of claim 1, wherein said first moiety is N-arginylphosphatidylethanolamine.

3. A method to transfer at least one nucleic acid into cells comprising:
   (a) forming a composition of claim 1 in an aqueous solution so to produce a claim or liposome containing solution;
   (b) contacting the micell or liposome containing solution with the cells so as to allow transfer of the nucleic acid into the cells.

4. A method of claim 3, wherein the nucleic acid delivered is a polynucleotide.

5. A method of claim 4, wherein the nucleic acid delivered is DNA.

6. A method of claim 4, wherein the nucleic acid delivered is RNA.

7. A method of claim 3, wherein the nucleic acid delivered is an oligonucleotide.

8. A composition of claim 2, wherein no second moiety is present.

9. A composition of claim 8, wherein said nucleic acid is an oligonucleotide.

10. A composition of claim 8, wherein said nucleic acid is a polynucleotide.

11. A composition of claim 10, wherein said nucleic acid is DNA.

12. A composition of claim 10, wherein said nucleic acid is RNA.

13. A composition of claim 1, wherein said nucleic acid is an oligonucleotide.

14. A composition of claim 1, wherein said nucleic acid is a polynucleotide.

15. A composition of claim 1, wherein said nucleic acid is DNA.

16. A composition of claim 1, wherein said nucleic acid is RNA.

* * * * *